(12) United States Patent
Wadhwa et al.

(10) Patent No.: US 10,646,532 B2
(45) Date of Patent: May 12, 2020

(54) METHOD FOR PREPARING WATER EXTRACT OF ASHWAGANDHA LEAVES WHICH HAS ENHANCED ANTI-CANCER ACTIVITY UTILIZING CYCLODEXTRIN, AND PHARMACEUTICAL COMPOSITION CONTAINING ASHWAGANDHA LEAVES

(71) Applicants: National Institute of Advanced Industrial Science and Technology, Chiyoda-ku, Tokyo (JP); Cyclochem Co., Ltd., Kobe-shi, Hyogo (JP)

(72) Inventors: Renu Wadhwa, Tsukuba (JP); Sunil Kaul, Tsukuba (JP)

(73) Assignees: National Institute of Advanced Industrial Science and Technology, Tokyo (JP); Kaul-Tech Co., Ltd., Ibaraki (JP)

( * ) Notice: Subject to any disclaimer, the term of this patent is extended or adjusted under 35 U.S.C. 154(b) by 719 days.

(21) Appl. No.: 15/115,345

(22) PCT Filed: Jan. 29, 2015

(86) PCT No.: PCT/JP2015/052431
§ 371 (c)(1),
(2) Date: Jul. 29, 2016

(87) PCT Pub. No.: WO2015/115512
PCT Pub. Date: Aug. 6, 2015

(65) Prior Publication Data
US 2017/0007659 A1    Jan. 12, 2017

(30) Foreign Application Priority Data

Jan. 29, 2014 (JP) .................. 2014-014389
Nov. 12, 2014 (JP) .................. 2014-229652

(51) Int. Cl.
| A61K 36/81 | (2006.01) |
| A61K 47/40 | (2006.01) |
| A61K 9/08  | (2006.01) |
| A61K 9/16  | (2006.01) |

(52) U.S. Cl.
CPC .......... *A61K 36/81* (2013.01); *A61K 9/08* (2013.01); *A61K 9/16* (2013.01); *A61K 47/40* (2013.01); *A61K 2236/331* (2013.01); *A61K 2236/53* (2013.01)

(58) Field of Classification Search
CPC .................................................. A61K 36/81
USPC ..................................................... 424/774
See application file for complete search history.

(56) References Cited

U.S. PATENT DOCUMENTS

| 6,538,020 B2 | 3/2003 | Joshi-Hangal et al. |
| 9,421,267 B2 | 8/2016 | Yacoby-Zeevi et al. |
| 9,872,914 B2 | 1/2018 | Inaba et al. |
| 2012/0231079 A1* | 9/2012 | Gupta .................. A61K 9/0024 424/486 |
| 2013/0039883 A1* | 2/2013 | Sayers ................. A61K 31/047 424/85.1 |

FOREIGN PATENT DOCUMENTS

| EP | 2260855 | 12/2010 |
| JP | 2003-512416 | 4/2003 |
| JP | 2006-111534 | 4/2006 |
| JP | 2013-545745 | 12/2013 |
| WO | 2005/082392 | 9/2005 |
| WO | 2009/110546 | 9/2009 |
| WO | WO-2009110546 A1 * | 9/2009 ............. A61K 36/18 |
| WO | 2013/125617 | 8/2013 |

OTHER PUBLICATIONS

Kamigauchi et al. "Inclusion Effect and Structural Basis of Cyclodextrins for Increased Extraction of Medicinal Alkaloids from Natural Medicines" (Chem. Pharm. Bull, 55(5) 729-733 (2007)). (Year: 2007).*

Wadhwa, Renu, et al., "Water Extract of Ashwagandha Leaves Has Anticancer Activity: Identification of an Active Component and Its Mechanism of Action", PLOS One, 2013, vol. 3, No. 10, pp. 1-11.

Kamigauchi, Miyoko, et al., "Inclusion Effect and Structural Basis of Cyclodextrins for Increased Extraction of Medicinal Alkaloids from Natural Medicines", Chemical and Pharmaceutical Bulletin, 2007, vol. 55, No. 5, pp. 729-733.

Isacchi B., et al., "Pharmacological in vivo Test to Evaluate the Bioavailability of some of St. John's Wort Innovative Oral Preparations", Phytotherapy Research, 2009, vol. 23, No. 2., pp. 197-205.

(Continued)

*Primary Examiner* — Michael Barker
*Assistant Examiner* — Deborah A Davis
(74) *Attorney, Agent, or Firm* — McCarter & English, LLP (57) ABSTRACT

It is an object of the present invention to provide a method for preparing a water extract of ashwagandha, which comprises increasing the amounts of withanone and withaferin A contained as active ingredients in the water extract of ashwagandha leaves. In addition, it is another object of the present invention to more economically and simply provide a pharmaceutical composition comprising ashwagandha leaves.

The present invention relates to a method for preparing a water extract of ashwagandha leaves, which comprises extracting ashwagandha leaves with water in the presence of cyclodextrin, and a method for enhancing the anticancer activity of the water extract of ashwagandha leaves. The present invention also relates to a pharmaceutical composition for treating or preventing cancer, comprising the water extract of ashwagandha leaves. The present invention further relates to a pharmaceutical composition comprising dry powders of ashwagandha leaves and cyclodextrin.

2 Claims, 6 Drawing Sheets

(56) References Cited

OTHER PUBLICATIONS

Widodo, Nashi, et al., Selective Killing of Cancer Cells by Leaf Extract of Ashwagandha: Components, Activity and Pathway Analyses, Cancer Letters, 2008, vol. 262, No. 1, p. 37-47.
International Search Report relating to International Application No. PCT/JP2015/052431, dated Mar. 31, 2015.
Withania—English abstract of the Encyclopedia of World Medicinal Plants, Seibundo Shinkosha Publishing Co., Ltd. 2000, p. 150, Author: Andrew Chevallier, 1 Page (Japanese language 2 Pages).
Japanese Office Action of co-pending Japanese Application No. 2015-559996, dated Jan. 8, 2019—4 Pages.

* cited by examiner

(a) Control (b) Dry powders of ashwagandha leaves (c) Dry powders of ashwagandha leaves + γ-cyclodextrin (1 : 0.5)

(d) Dry powders of ashwagandha leaves + γ-cyclodextrin (1 : 0.25)

Fig. 6

METHOD FOR PREPARING WATER EXTRACT OF ASHWAGANDHA LEAVES WHICH HAS ENHANCED ANTI-CANCER ACTIVITY UTILIZING CYCLODEXTRIN, AND PHARMACEUTICAL COMPOSITION CONTAINING ASHWAGANDHA LEAVES

RELATED APPLICATIONS

This application is a national stage application filed under 35 USC 371 of PCT/JP2015/052431, filed Jan. 29, 2015, which claims the benefit of Japanese Patent Application No. 2014-014389, filed Jan. 29, 2014, and Japanese Patent Application No. 2014-229652, filed Nov. 12, 2014 all of which are incorporated herein, in entirety, by reference.

TECHNICAL FIELD

The present invention relates to a method for preparing a water extract of ashwagandha leaves and a method for enhancing the anticancer activity of the water extract of ashwagandha leaves. The present invention also relates to a pharmaceutical composition for treating or preventing cancer, comprising the water extract of ashwagandha leaves. The present invention further relates to a pharmaceutical composition comprising dry powders of ashwagandha leaves and cyclodextrin.

BACKGROUND ART

Cancer is the leading cause of death over the world, and it accounts for a high percentage. The survival rate of cancer patients has been increased as a result of progression of cancer diagnosis methods and cancer treatment methods. However, it is still difficult for people living in developing countries, which account for 75% of the entire global population, to receive advanced cancer therapy. As such, it has been desired to develop an inexpensive cancer therapy.

In contrast with advanced medical treatments, natural treatments of using herbs and the like have been known from old times. Ayurveda is one type of natural treatment that has practiced in India from B. C. Roots of the medical herb ashwagandha (scientific name: *Withania somnifera*; which is also referred to an Indian carrot, Indian *ginseng* or Winter cherry), which are used in the Ayurveda, have been known to have a nourishment-enhancing action, a health-promoting action and the like.

The present inventors had previously found that an alcohol extract of ashwagandha leaves exhibits an anticancer activity (Patent Literature 1). Such an alcohol extract of ashwagandha leaves comprises, as active ingredients, withanolides such as withanone and withaferin A represented by the following formulae:

[Formula 1]

Withaferin A

Withanone

Thus, the alcohol extract of ashwagandha leaves kills cancer cells based on mechanisms such as apoptosis or growth inhibition. In an in vitro test, withanone exhibits selective cytotoxicity to cancer cells, whereas withaferin A has effects even on normal cells. By adding withanone and withaferin A to a cell culture solution, normal cells can be protected from the cytotoxicity of withaferin A by the action of withanone.

Also, the present inventors had previously found that a water extract of ashwagandha leaves has an anticancer activity (Patent Literature 2). In such a water extract of ashwagandha leaves, the contents of withanone and withaferin A are low, and triethylene glycol has been known to be a main anticancer component (Non Patent Literature 1).

CITATION LIST

Patent Literature

Patent Literature 1: International Publication WO 2005/82392
Patent Literature 2: International Publication WO 2009/110546

Non Patent Literature

Non Patent Literature 1: Renu Wadhwa et al: PLOS ONE 2013, Vol. 8, Issue 10, e77189

SUMMARY OF INVENTION

Technical Problem

As described above, in a water extract of ashwagandha leaves, the contents of withanone and withaferin A as active ingredients are low.

As such, it is an object of the present invention to provide a method for preparing a water extract of ashwagandha leaves, by which the amounts of withanone and withaferin A contained as active ingredients therein can be increased. In addition, it is another object of the present invention to more economically and simply provide a pharmaceutical composition comprising ashwagandha leaves.

Solution to Problem

As a result of intensive studies directed towards achieving the aforementioned objects, the present inventors have found that the amounts of withanone and withaferin A contained as active ingredients in a water extract of ashwagandha leaves can be increased with the use of cyclodextrin, and also that a pharmaceutical composition comprising ashwagandha leaves can be more economically and simply provided by using dry powders of ashwagandha leaves and cyclodextrin, thereby completing the present invention.

Specifically, the gist of the present invention is as follows.
(1) A method for preparing a water extract of ashwagandha leaves, which comprises extracting ashwagandha leaves with water in the presence of cyclodextrin.
(2) The preparation method according to (1) above, wherein the cyclodextrin is at least one selected from the group consisting of α-cyclodextrin, β-cyclodextrin, γ-cyclodextrin, hydroxypropyl-β-cyclodextrin, sulfobutyl ether-β-cyclodextrin, and branched cyclodextrin.
(3) A method for enhancing the anticancer activity of a water extract of ashwagandha leaves, using cyclodextrin.
(4) A pharmaceutical composition for treating or preventing cancer, which comprises the water extract of ashwagandha leaves obtained by the preparation method according to (1) or (2) above.
(5) A pharmaceutical composition for treating or preventing cancer, which comprises a composition obtained by mixing a water extract of ashwagandha leaves with cyclodextrin.
(6) A pharmaceutical composition for use in simultaneous, separate or sequential administration, wherein the pharmaceutical composition comprises dry powders of ashwagandha leaves and cyclodextrin.
(7) The pharmaceutical composition according to (6) above, which is for use in treating or preventing cancer.
(8) The pharmaceutical composition according to (6) or (7) above, wherein the cyclodextrin is γ-cyclodextrin.

The present description includes part or all of the contents as disclosed in the descriptions and/or drawings of Japanese Patent Application Nos. 2014-014389 and 2014-229652, which are priority documents of the present application.

Advantageous Effects of Invention

According to the present invention, there is provided a method for preparing a water extract of ashwagandha leaves, by which the amounts of withanone and withaferin A contained as active ingredients therein have been increased. In addition, it becomes possible to more economically and simply provide a pharmaceutical composition comprising ashwagandha leaves.

BRIEF DESCRIPTION OF DRAWINGS

FIG. 5(*a*)-(*d*) each include a view showing a change in body weight in an in vivo antitumor assay using mice.

DESCRIPTION OF EMBODIMENTS

Hereinafter, preferred embodiments of the present invention will be described in detail.

1. Method for Preparing Water Extract of Ashwagandha Leaves

The present invention relates to a method for preparing a water extract of ashwagandha leaves, using cyclodextrin. The method for preparing a water extract of ashwagandha leaves of the present invention is characterized in that it comprises extracting ashwagandha leaves with water in the presence of cyclodextrin. By extracting ashwagandha leaves with water in the presence of cyclodextrin, the contents of withanone and withaferin A in the obtained water extract can be increased, when compared with the case of not using cyclodextrin.

In the method of the present invention, *Withania somnifera* (scientific name) is used as ashwagandha. Such ashwagandha is not limited to those growing in nature, and it may also be ashwagandha that has been cultured in vitro. However, the composition of components contained in the ashwagandha leaves is considered to be slightly different depending on the growing area thereof, the age of a tree thereof, etc. Thus, in order to obtain the water extract of ashwagandha leaves of the present invention, it is desirable to use 2- to 4-year old plants that have been cultivated from seeds in India. The ashwagandha leaves may be any one of fresh leaves immediately after harvesting, dried products of such fresh leaves, and roasted products of such fresh leaves. Among others, the dried leaves are desirable. The ashwagandha leaves may be used as are, but the leaves are preferably used after they have been treated as appropriate, and for example, the leaves can be used in the form of powders.

The cyclodextrin (CD) used in the method of the present invention is not particularly limited. Examples of the cyclodextrin (CD) that can be used herein include α-cyclodextrin, β-cyclodextrin, γ-cyclodextrin, and a derivative thereof. Examples of the aforementioned derivative include branched cyclodextrin and chemically modified cyclodextrin. An example of the branched cyclodextrin is glycosylated CD, in which a glycosylated chain is bound to cyclodextrin by an enzymatic reaction. More specific examples of the branched cyclodextrin include monosaccharide- or disaccharide-modified CD, such as glucosyl-CD, maltosyl-CD, galactosyl-CD or mannosyl-CD. Examples of the chemically modified cyclodextrin include partially methylated CD, hydroxypropylated CD, sulfobutyletherified CD, acetylated CD, and monochlorotriazinated CD. In the method of the present invention, α-cyclodextrin, β-cyclodextrin, γ-cyclodextrin, hydroxypropyl β-cyclodextrin, sulfobutyl ether β-cyclodextrin or branched cyclodextrin is preferably used. Among these, β-cyclodextrin is particularly preferable. If β-cyclodextrin is used, the contents of withanone and withaferin A are increased in the obtained water extract of ashwagandha leaves.

The cyclodextrin used in the method of the present invention is preferably used in the form of an aqueous solution.

In a preferred embodiment of the present invention, the water extract of ashwagandha leaves of the present invention can be obtained by mixing ashwagandha leaves with a cyclodextrin aqueous solution, and then subjecting the obtained slurry to centrifugation and/or filtration.

The mixing of ashwagandha leaves with cyclodextrin is not particularly limited. The mixing of ashwagandha leaves with cyclodextrin can be achieved, for example, by adding ashwagandha leaves to a cyclodextrin aqueous solution, and then treating the obtained mixture at a temperature of 5° C. to 60° C. at a rotation number of 10 to 200 rpm for 6 to 100 hours.

2. Pharmaceutical Composition for Treating or Preventing Cancer, Comprising Water Extract of Ashwagandha Leaves The present invention also relates to a pharmaceutical composition for treating or preventing cancer, which comprises a water extract of ashwagandha leaves. The pharmaceutical composition of the present invention comprises a water-soluble substance derived from ashwagandha leaves and cyclodextrin. Preferably, the pharmaceutical composition of the present invention comprises a complex of a water-soluble substance derived from ashwagandha leaves and cyclodextrin. The complex of a water-soluble substance derived from ashwagandha leaves and cyclodextrin of the present invention includes not only a complex obtained by combining the substances in vitro, but also a complex obtained by administering the substances to a target, separately, and then combining them in vivo.

The pharmaceutical composition of the present invention can be obtained by mixing a water extract of ashwagandha leaves with cyclodextrin. Herein, with regard to the mixing of a water extract of ashwagandha leaves with cyclodextrin, after a water extract of ashwagandha leaves has been prepared, the water extract may be mixed with cyclodextrin. Otherwise, preparation of a water extract of ashwagandha leaves and the mixing of the water extract with cyclodextrin may also be carried out simultaneously. Specifically, the pharmaceutical composition of the present invention can be obtained by mixing a water extract of ashwagandha leaves, which has been extracted without using cyclodextrin, with cyclodextrin, or by extracting ashwagandha leaves with water in the presence of the cyclodextrin as mentioned above.

When the pharmaceutical composition of the present invention is obtained by preparing a water extract of ashwagandha leaves and then mixing the water extract with cyclodextrin, the present pharmaceutical composition can be obtained, for example, by adding a predetermined amount of the water extract to an aqueous solution or suspension of 5% to 20% cyclodextrin, then stirring the mixed solution for several minutes to several tens of hours, at room temperature or under heating, and then recovering the obtained precipitate by centrifugation or the like.

When a water extract of ashwagandha leaves is prepared without using cyclodextrin, this water extract is not particularly limited, and can be obtained by a method which comprises adding ashwagandha leaves to water and then treating them at a temperature of 20° C. to 70° C. for 6 to 100 hours, or by a method which comprises adding ashwagandha leaves to water, then heating them to a temperature of 70° C. to 100° C., and then cooling the reaction mixture to a temperature of 1° C. to 30° C.

The type of the cyclodextrin to be mixed with a water extract of ashwagandha leaves is not particularly limited, and the above-described α-cyclodextrin, β-cyclodextrin, γ-cyclodextrin, or a derivative thereof can be used. Among others, α-cyclodextrin, β-cyclodextrin, γ-cyclodextrin, hydroxypropyl β-cyclodextrin, sulfobutyl ether β-cyclodextrin, or branched cyclodextrin is preferable, and further, γ-cyclodextrin is particularly preferable. Since the ratio of withanone/withaferin A in the obtained pharmaceutical composition becomes high when γ-cyclodextrin is used, the pharmaceutical composition has a high anticancer activity.

In the present description, the term "anticancer activity" is used to mean an activity of suppressing the growth of cancer, and more specifically, that the pharmaceutical composition has cytotoxicity on cancer cells, and has actions such as suppression of the growth and infiltration of cancer cells, activation of the tumor suppressor protein p53 or pRB, inhibition of telomerase activity, and induction of differentiation. The pharmaceutical composition of the present invention can be used to treat or prevent cancer, alone or in combination with chemotherapy using other anticancer agents, radiation therapy, or the like.

The term "cancer" is used in the present description to include all of: cancers developed in epithelial tissues, such as pancreatic cancer, stomach cancer, colon cancer, kidney cancer, liver cancer, bone marrow cancer, adrenal cancer, skin cancer, melanoma, lung cancer, small intestine cancer, prostate cancer, testicular cancer, uterine cancer, breast cancer or ovary cancer; solid cancers including sarcomas that are malignant tumors developed in non-epithelial sites such as muscle or bone; and other humoral cancers such as leukemia or malignant lymphoma. Among others, the pharmaceutical composition of the present invention is effective for the treatment or prevention of solid cancers.

With regard to the pharmaceutical composition of the present invention, a water extract of ashwagandha leaves serving as an active ingredient, together with a pharmaceutically acceptable carrier, may be formulated into any given dosage form, as necessary, and thus, various administration forms can be adopted for the present pharmaceutical composition. Specific examples of the dosage form include a tablet, a capsule, a liquid agent, a dusting agent, a powdered agent, a granule, and an injection agent. The administration route may be either an oral administration route or a parenteral administration route. Examples of the parenteral administration route include intravenous administration, subcutaneous administration, intramuscular administration, and intraperitoneal administration.

Examples of the pharmaceutically acceptable carrier, which is used in solid formulations, include an excipient, a binder, a disintegrator, and a lubricant. Examples of the pharmaceutically acceptable carrier, which is used in liquid formulations, include a solvent, a solubilizer, a suspending agent, a tonicity agent, a buffer, and a soothing agent. In addition, formulation additives such as an antiseptic, an antioxidant, a coloring agent, a sweetener or a stabilizer can also be used, as necessary.

When an oral solid formulation is prepared, an excipient, a binder, a disintegrator, a lubricant, a coloring agent, a flavoring agent and the like are added to a water extract of ashwagandha leaves serving as an active ingredient, as necessary, and thereafter, the obtained mixture can be processed into a tablet, a granule, a capsule, etc. according to an ordinary method.

3. Method for Enhancing Anticancer Activity of Water Extract of Ashwagandha Leaves, Using Cyclodextrin The present invention also relates to a method for enhancing the anticancer activity of a water extract of ashwagandha leaves, using cyclodextrin. In the method of the present invention, by extracting ashwagandha leaves with water in the presence of cyclodextrin, the contents of withanone and withaferin A in the obtained water extract of ashwagandha leaves are increased, and thereby, the anticancer activity of the extract can be enhanced. Moreover, even when cyclodextrin is added to a water extract of ashwagandha leaves after completion of the preparation of the water extract, the contents of withanone and withaferin A in the obtained mixture are increased, and thereby, the anticancer activity of the extract can be enhanced.

4. Pharmaceutical Composition Comprising Dry Powders of Ashwagandha Leaves and Cyclodextrin The present invention also relates to a pharmaceutical composition comprising dry powders of ashwagandha leaves and cyclodextrin. By using dry powders of ashwagandha leaves, a pharmaceutical composition comprising ashwagandha leaves can be economically and simply prepared. Further, by using such dry powders of ashwagandha leaves, components contained in ashwagandha leaves can be stabilized, and bioavailability can be thereby improved.

The dry powders of ashwagandha leaves can be obtained by drying ashwagandha leaves and crushing the dried ashwagandha leaves. The drying means is not particularly limited, as long as it does not impair the pharmacological effects of ashwagandha leaves. Examples of such a drying means include an air heating dryer, a heating dryer that does not involve ventilation, and a microwave vacuum dryer. Drying conditions are different depending on the condition of leaves as raw materials. The drying temperature is generally from 25° C. to 70° C. The crushing means is not particularly limited, and it can be a crusher such as a mixer, a pin mill or a stone-type water cooling crushing machine.

The dry powders of ashwagandha leaves may be dissolved in a solvent. The type of such a solvent is not particularly limited, and examples of the solvent include water and an organic solvent.

The type of cyclodextrin is not particularly limited. Examples of cyclodextrin include α-cyclodextrin, β-cyclodextrin, γ-cyclodextrin, hydroxypropyl-β-cyclodextrin, sulfobutyl ether-β-cyclodextrin, and branched cyclodextrin. Among these, γ-cyclodextrin is preferably used. By using γ-cyclodextrin, the pharmaceutical composition can have a high anticancer activity.

The pharmaceutical composition comprising the dry powders of ashwagandha leaves and cyclodextrin is able to enhance, for example, anticancer activity, anti-aging activity, antioxidative activity, neuronal differentiation-inducing activity, muscle differentiation-inducing activity, anti-pigmentation activity, anti-inflammatory activity, antiarthritic activity, antidiabetic activity, anti-stress activity and tonic effect, which ashwagandha leaves have.

The above-described pharmaceutical composition is preferably used for cancer therapy, anti-aging, antioxidation, pigmentation inhibition, inflammation inhibition, the treatment of arthritis, the treatment of diabetes and stress suppression, and also for prevention of the aforementioned symptoms. The pharmaceutical composition is more preferably used for cancer therapy and prevention thereof.

The pharmaceutical composition of the present invention is administered simultaneously, separately, or sequentially. The term "simultaneously" is used in the present description to mean that an agent is administered almost at the same time as another agent. The term "separately" is used herein to mean that the agents are administered at different time points, separately, and for example, it is a case where one agent is administered on the first day and the other agent is administered on the second day. The term "sequentially" is used herein to mean that the agents are administered in a certain order, and for example, it is a case where one agent is firstly administered, and the other agent is then administered after a predetermined time has passed. The administration route may be either an oral administration route or a parenteral administration route. Examples of the parenteral administration route include intravenous administration, subcutaneous administration, intramuscular administration, and intraperitoneal administration.

With regard to the pharmaceutical composition of the present invention, dry powders of ashwagandha leaves serving as an active ingredient, together with a pharmaceutically acceptable carrier, may be formulated into any given dosage form, as necessary, and thus, various administration forms can be adopted for the present pharmaceutical composition. Specific examples of the dosage form include a tablet, a capsule, a liquid agent, a dusting agent, a powdered agent, a granule, and an injection agent.

Examples of the pharmaceutically acceptable carrier, which is used in solid formulations, include an excipient, a binder, a disintegrator, and a lubricant. Examples of the pharmaceutically acceptable carrier, which is used in liquid formulations, include a solvent, a solubilizer, a suspending agent, a tonicity agent, a buffer, and a soothing agent. In addition, formulation additives such as an antiseptic, an antioxidant, a coloring agent, a sweetener or a stabilizer can also be used, as necessary.

EXAMPLES

Hereinafter, the present invention will be more specifically described in the following examples. However, these examples are not intended to limit the technical scope of the present invention.

1. Use of Water Extract of Ashwagandha Leaves and Complex Thereof 1-1. Preparation of Water Extract of Ashwagandha Leaves and Complex Thereof Example 1

Preparation of water extract of ashwagandha leaves using α-cyclodextrin 100 mL of an aqueous solution of 10% α-cyclodextrin (CAVAMAX (registered trademark) W6 FOOD, manufactured by Wacker) was added to 5 g of dry powders of ashwagandha (*Withania somnifera*) leaves (native to India, iGENE), and the obtained mixture was then stirred at room temperature at 60 rpm for 20 hours. Thereafter, the obtained slurry was centrifuged at 3500 rpm for 5 minutes, and a supernatant was then filtered through a 0.2-μm filter to obtain a water extract of ashwagandha leaves. The obtained water extract was directly used in the subsequent test.

Example 2

Preparation of Water Extract of Ashwagandha Leaves Using β-Cyclodextrin

A water extract of ashwagandha leaves was obtained by the same method of that of Example 1, with the exception that an aqueous solution of 2% 3-cyclodextrin (CAVAMAX (registered trademark) W7 FOOD, manufactured by Wacker) was used instead of the 10% α-cyclodextrin aqueous solution.

Example 3

Preparation of Water Extract of Ashwagandha Leaves Using γ-Cyclodextrin

A water extract of ashwagandha leaves was obtained by the same method of that of Example 1, with the exception that an aqueous solution of 10% γ-cyclodextrin (CAVAMAX (registered trademark) W8 FOOD, manufactured by Wacker) was used instead of the 10% α-cyclodextrin aqueous solution.

Comparative Example 1

Preparation of Water Extract of Ashwagandha Leaves, in which Cyclodextrin is not Used 100 mL of sterile water was added to 5 g of dry powders of ashwagandha leaves, and thereafter, the obtained mixture was slowly stirred at 40° C. overnight. Thereafter, the temperature of the obtained slurry mixture was returned to room temperature, and was then filtered through a filter (Whatman; Grade No. 4). The resultant was centrifuged at 10,000 rpm for 20 minutes, and a supernatant was then subjected to sterile filtration through a 0.45-μm filter to obtain a water extract of ashwagandha leaves. The obtained water extract was directly used in the subsequent test.

Example 4

Complex of Water Extract of Ashwagandha Leaves and γ-Cyclodextrin

To a water extract of ashwagandha leaves that had been obtained by the same method as that of Comparative Example 1, γ-cyclodextrin was added to result in a concentration of 10%. The obtained mixture was stirred at room temperature at 60 rpm for 20 hours, and was then centrifuged at 3500 rpm for 5 minutes. The obtained precipitate was recovered as a complex of a water extract of ashwagandha leaves and γ-cyclodextrin.

1-2. Analysis of Components

Figure 1:
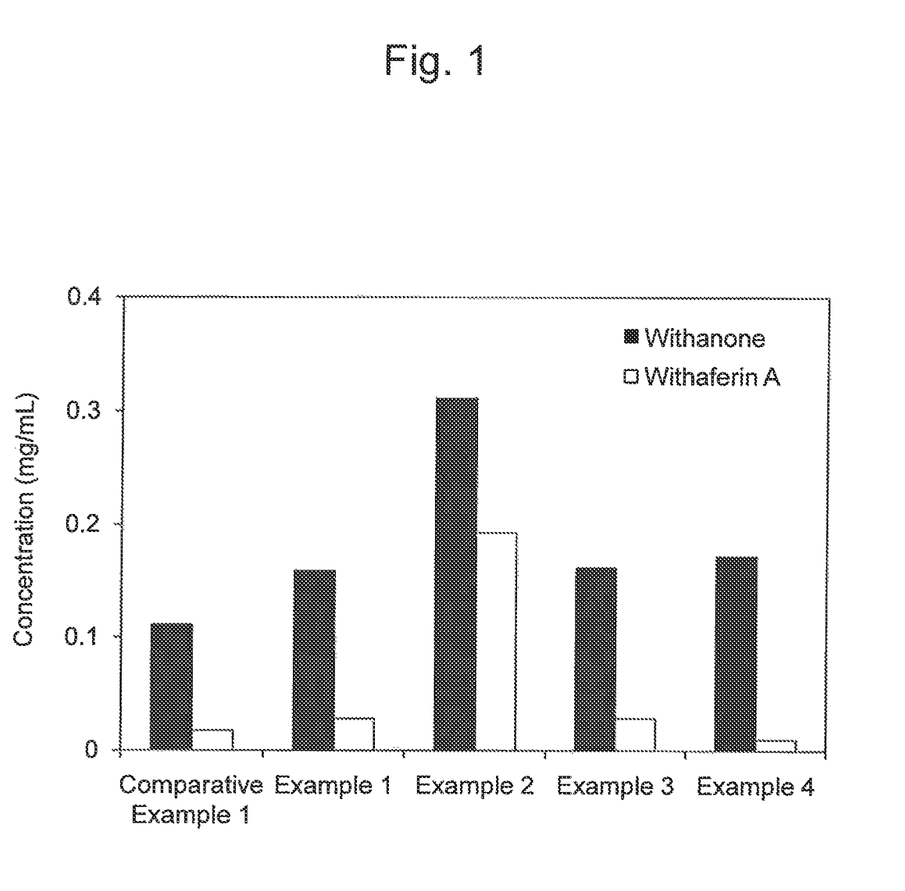
FIG. 1 is a view showing the contents of withanone and withaferin A in each of the water extracts of Examples 1-3 and Comparative Example 1 and the complex of Example 4.

The amounts of withanone and withaferin A, which were contained in each of the water extracts obtained in Example 1-3 and Comparative Example 1 and the complex obtained in Example 4, were measured by HPLC analysis. In the case of the extracts of Example 1-3 and Comparative Example 1, the obtained water extracts were directly subjected to the HPLC analysis, and the contents of withanone and withaferin A were each calculated using their standard preparations, respectively. In the case of the complex of Example 4, the complex was dissolved in dimethyl sulfoxide (DMSO), and the obtained solution was then subjected to HPLC analysis, so that the contents of withanone and withaferin A were each calculated using their standard preparations, respectively. The HPLC conditions were as follows:

Column: Luna 5u C18(2) 100A (5 μm, 150 (L)×4.6 (D))
Column oven: 45° C.
Solution A: 1% methanol
Solution B: methanol:ethanol:i-propanol=52.25:45.30:2.45
Gradient program:
Initial: A 65% (B 35%)→30 minutes: A 55% (B 45%)
Flow rate: 1 mL/min
Detector wavelength: 220 nm The results are shown in FIG. 1. As shown in FIG. 1, it was found that the contents of withanone and withaferin A in the water extract became higher in the case of extraction in the presence of cyclodextrin (Examples 1-3) than in the case of extraction without cyclodextrin (Comparative Example 1). In particular, in the case of using β-cyclodextrin (Example 2), the contents of withanone and withaferin A became much higher than those in the case of not using cyclodextrin (Comparative Example 1). Moreover, the content of withanone in the complex of Example 4 was higher than in the case of not using cyclodextrin (Comparative Example 1). In all of the cases of Example 1-4 and Comparative Example 1, the content of withanone in the water extract or the complex was higher than the content of withaferin A therein. The complex of Example 4 exhibited the highest withanone/withaferin A ratio.

1-3. In Vitro Cancer Cell Cytotoxicity Assay Performed on Cancer Cells

Human osteosarcoma cells (U2OS, obtained from American Type Culture Collection (ATCC, Manassas, Va.)) were cultured with Dulbecco's Modified Eagle's Medium (DMEM, Invitrogen), to which 10% fetal bovine serum had been added, in a humidified incubator (at 37° C., in 5% $CO_2$). After the cells had been cultured to 40% to 60% confluence, the resulting cells were treated with each of predetermined amounts of the water extracts of Example 1-3 and Comparative Example 1 and the complex of Example 4. The treatment was carried out on the cells, typically over 48 hours, while culturing the cells at 37° C.

The cytotoxicity of each of the water extracts of Example 1-3 and Comparative Example 1 and the complex of Example 4 was evaluated by an assay using MTT (3-(4,5-dimethylthiazol-2-yl)-2,5-diphenyltetrazolium bromide) (Life Technologies). In this evaluation, cell survival was evaluated based on conversion of yellow MTT by mitochondrial dehydrogenases of living cells to purple formazan. After completion of the above-described treatment, MTT (0.5 mg/mL) was added to the cell culture medium, and the obtained mixture was then incubated for 4 hours. Subsequently, the medium containing MTT was removed, and 100 mL of DMSO was then added to each well, so that formazan crystals were completely dissolved therein. Using a multiplate spectrophotometer (TECAN Infinite M200Pro), the absorbance at 550 nm was measured.

Figure 2:
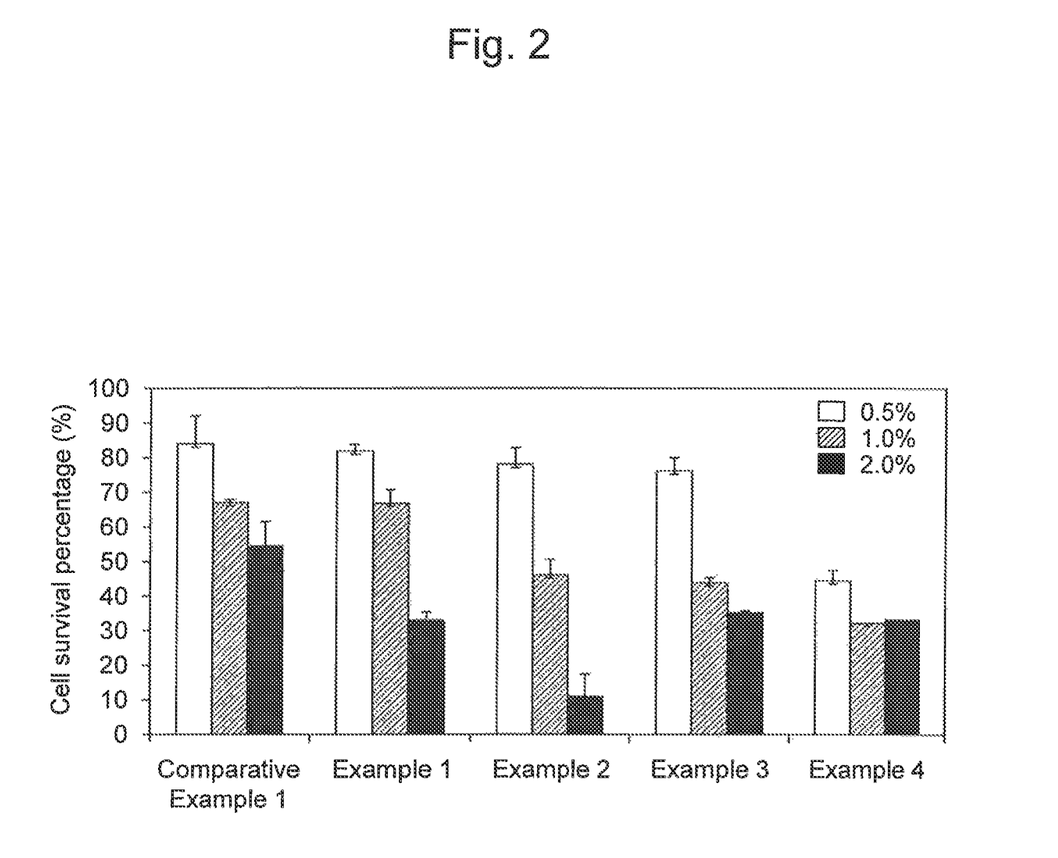
FIG. 2 is a view showing the results of an in vitro cancer cell cytotoxicity assay performed on cancer cells.

The results are shown in FIG. 2. As shown in FIG. 2, it was found that the water extracts of Example 1-3 and the complex of Example 4 exhibited higher cytotoxicity than the water extract of Comparative Example 1, and that the water extract of Example 2 obtained using β-cyclodextrin exhibited the highest cytotoxicity. Even if the complex of Example 4 was administered at a low dose, it exhibited sufficient cytotoxicity, in comparison to the water extract of Comparative Example 1.

1-4. In Vivo Antitumor Assay

Using subcutaneous xenograft model mice comprising HT1080 cells (human fibrosarcoma cells, obtained from JCRB Cell Bank), the complex of Example 4 and the water extract of Comparative Example 1 were subjected to an in vive antitumor assay.

HT1080 cells ($6 \times 10^6$ cells to 0.2 mL of growth medium) were subcutaneously injected into two site of each Balb/c nude mouse (4-week-old, female, purchased from CLEA Japan, Inc.). A control group was treated with 2% carboxymethyl cellulose; a water extract of Comparative Example 1 group was fed with the water extract of Comparative Example 1 at a dose of 500 mg/kg body weight/administration; and a complex of Example 4 group was fed with 500 mg of water extract of ashwagandha leaves (which was obtained by the same method as that of Comparative Example 1) and 0.625 mg of γ-cyclodextrin/kg body weight/ administration. The treatment was initiated on the 8th day after injection of the HT1080 cells, and the treatment was carried out 12 times every other day. Tumor formation was observed over 1 month, and the volume of subcutaneous tumor was calculated by the formula: V=L×W$^2$/2 (L: the length of tumor, W: the width of tumor). This assay was carried out using 3 mice from each group, and was repeated twice.

Figure 3:
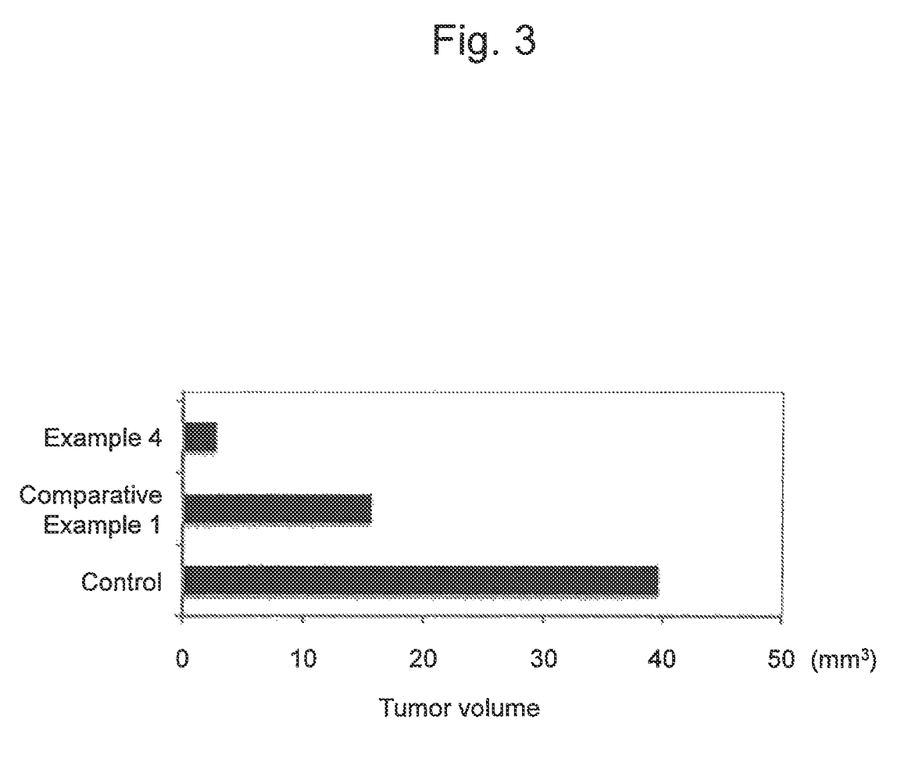
FIG. 3 is a view showing tumor volume in an in vivo antitumor assay using mice.
Figure 4:
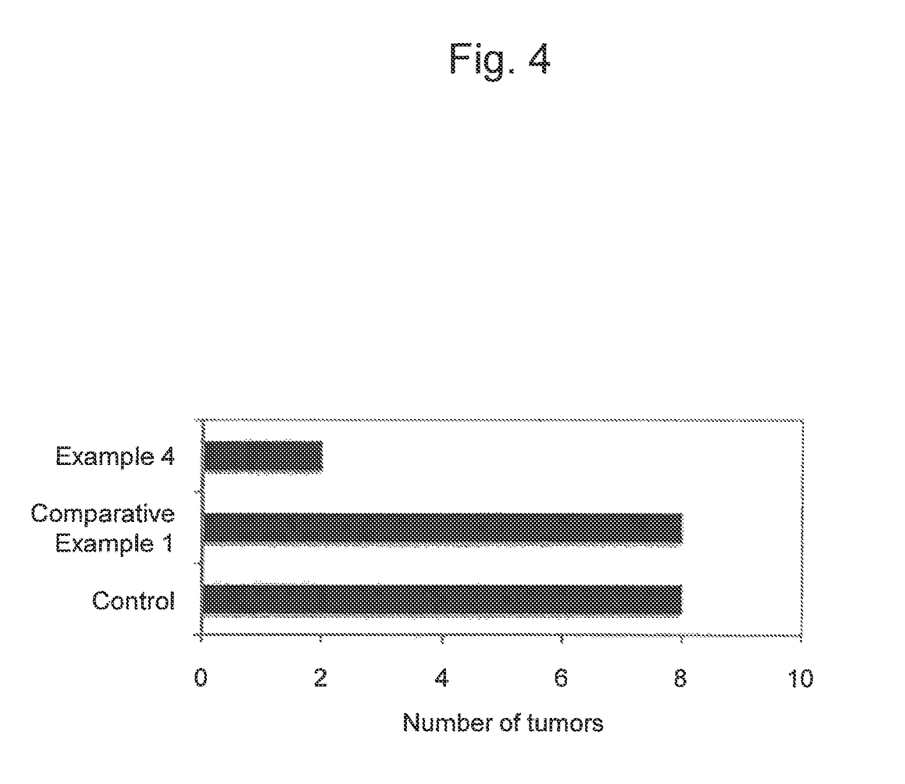
FIG. 4 is a view showing the number of tumors in an in vivo antitumor assay using mice.

The results regarding tumor volume are shown in FIG. 3, and the results regarding the number of tumors are shown in FIG. 4. As shown in FIG. 3 and FIG. 4, it was found that the number of tumors and the tumor volume were significantly reduced in the complex of Example 4 group, in comparison to the water extract of Comparative Example 1 group, and thus that tumor inhibitory effects were observed. From these results, it was demonstrated that the complex of Example 4 has a high anticancer activity, and also that the anticancer activity of a water extract of ashwagandha leaves can be enhanced by cyclodextrin.

2. Co-Administration of Dry Powders of Ashwagandha Leaves and γ-Cyclodextrin

Example 5

Preparation of Dry Powders of Ashwagandha Leaves

Dry powders of ashwagandha leaves were obtained by drying ashwagandha leaves comprising a high ratio of withanone/withaferin A at a temperature of 45° C. to 50° C., and then crushing the dried leaves. The obtained powders were sterilized by ultraviolet irradiation, and were then preserved in a vacuum pack at 28° C. or lower.

In Vivo Antitumor Assay

Using subcutaneous xenograft model mice comprising HT1080 cells (human fibrosarcoma cells, obtained from JCRB Cell Bank), a co-administration group of dry powders of ashwagandha leaves and γ-cyclodextrin and a single administration group of dry powders of ashwagandha leaves alone were each subjected to an in vivo antitumor assay.

HT1080 cells (6×10$^6$ cells to 0.2 mL of growth medium) were subcutaneously injected into two site of each Balb/c nude mouse (4-week-old, female, purchased from CLEA Japan, Inc.). A control group was treated with 1% carboxymethyl cellulose. The single administration group of dry powders of ashwagandha leaves was fed with dry powders of ashwagandha leaves at a dose of 50 mg/kg body weight/administration, together with 1% carboxymethyl cellulose. The co-administration group of dry powders of ashwagandha leaves and γ-cyclodextrin was fed with dry powders of ashwagandha leaves at a dose of 50 mg/kg body weight/administration and γ-cyclodextrin (CAVAMAX (registered trademark) W8 FOOD, manufactured by Wacker) at a dose of 12.5 mg or 25 mg/kg body weight/administration, in the same manner as in the case of the single administration group of dry powders of ashwagandha leaves. The treatment was initiated on the 3rd day after injection of the HT1080 cells, and the treatment was carried out every other day. Body weight and tumor formation were observed over 1 month, and the volume of subcutaneous tumor was calculated by the formula: V=L×W$^2$/2 (L: the length of tumor, W: the width of tumor). This assay was carried out using 5 mice from each group, and was repeated twice.

Figure 5:
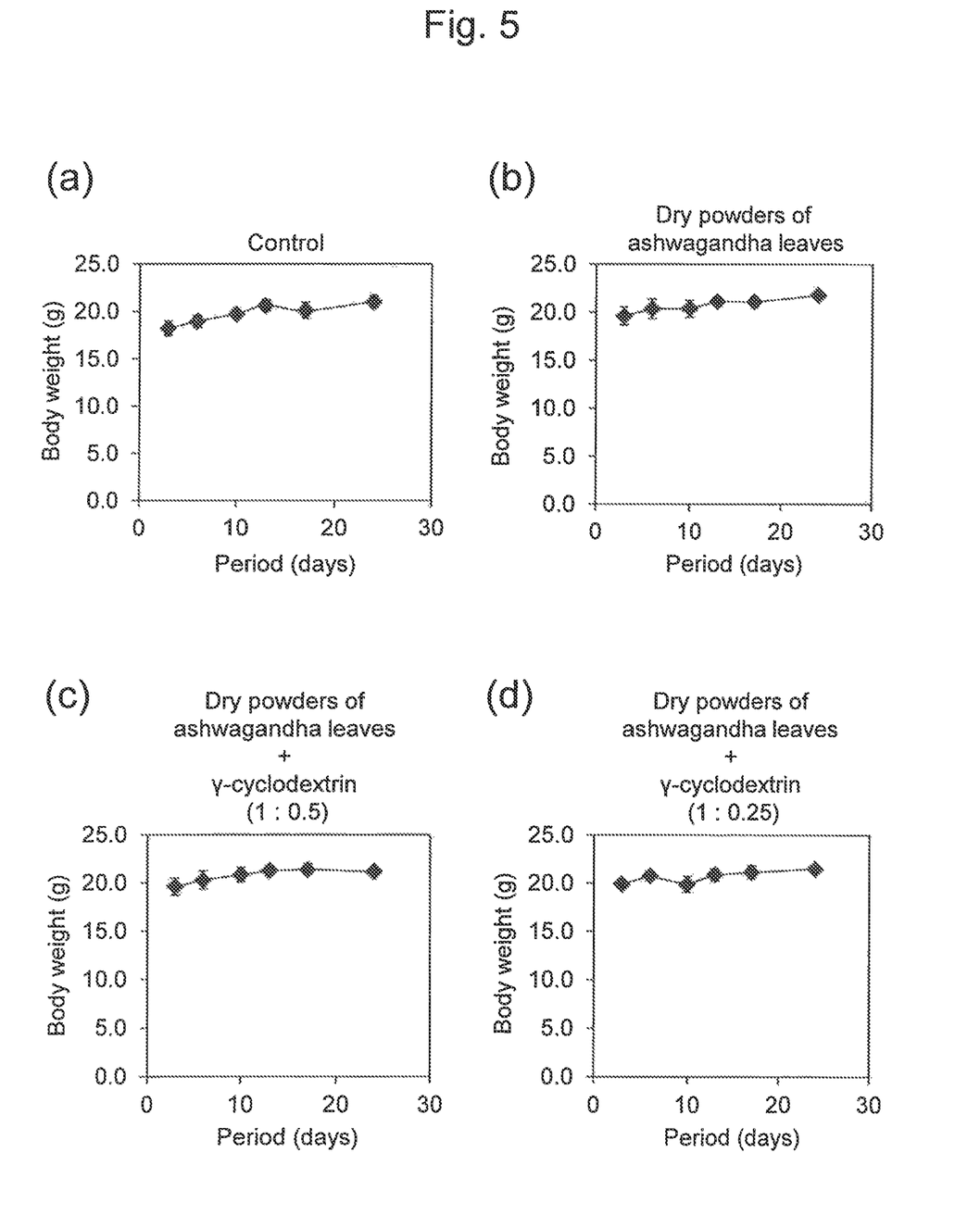

The results regarding changes in body weights are shown in FIG. 5(a) to (d). FIG. 5(a) shows a change in the body weight of the control group; FIG. 5(b) shows a change in the body weight of the single administration group of dry powders of ashwagandha leaves; FIG. 5(c) shows a change in the body weight of the co-administration group of dry powders of ashwagandha leaves and γ-cyclodextrin at a dose of 25 mg/kg body weight/administration; and FIG. 5(d) shows a change in the body weight of the co-administration group of dry powders of ashwagandha leaves and γ-cyclodextrin at a dose of 12.5 mg/kg body weight/administration. As shown in FIG. 5, it was found that there was observed no difference in terms of a change in the body weight between the single administration group of dry powders of ashwagandha leaves and the co-administration group of dry powders of ashwagandha leaves and γ-cyclodextrin.

Figure 6:
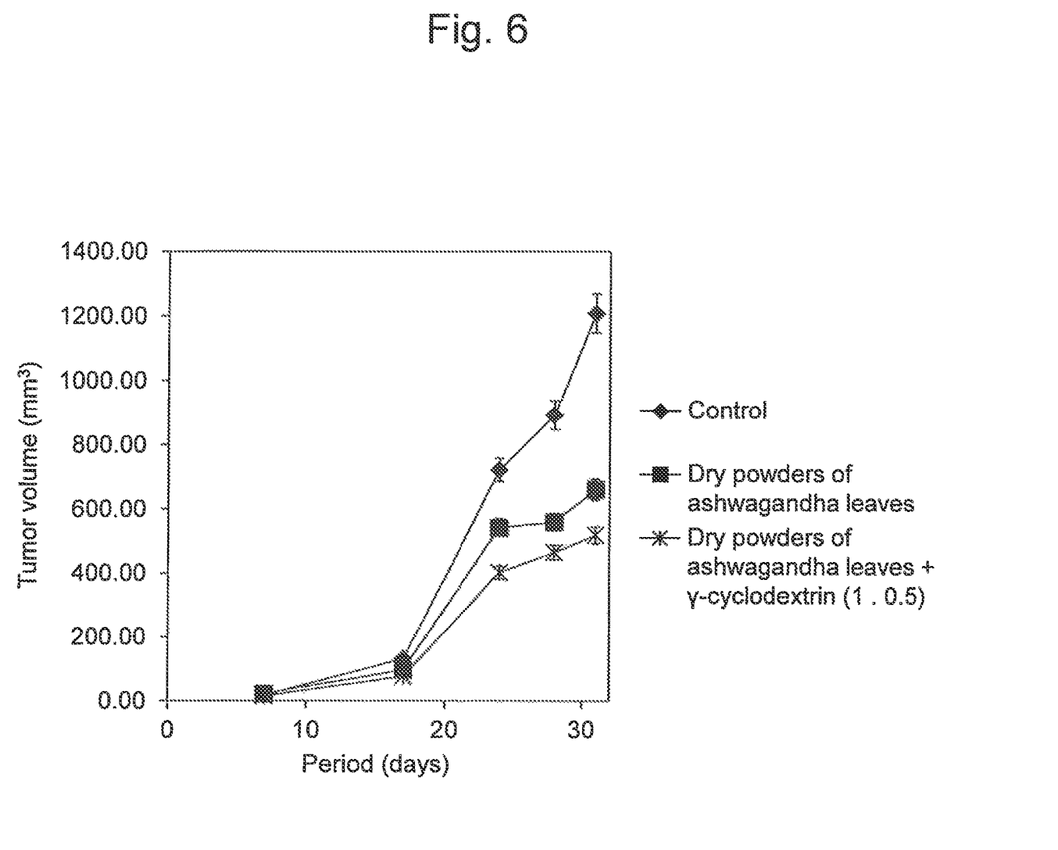
FIG. 6 is a view showing tumor volume in an in vivo antitumor assay using mice.

The results regarding tumor volume of the control group, the single administration group of dry powders of ashwagandha leaves, and the co-administration group of dry powders of ashwagandha leaves and γ-cyclodextrin at a dose of 25 mg/kg body weight/administration are shown in FIG. 6. As shown in FIG. 6, it was found that significant tumor growth inhibitory effects were observed in the single administration group of dry powders of ashwagandha leaves and in the co-administration group of dry powders of ashwagandha leaves and γ-cyclodextrin, in comparison to the control group, and also that the co-administration group of dry powders of ashwagandha leaves and γ-cyclodextrin exhibited a higher anticancer activity than the single administration group of dry powders of ashwagandha leaves did. HT1080 cells were injected into the caudal vein of the mice, and a similar analysis was carried out on tumor metastasized to the lung. The lung was observed 6 weeks after the injection of HT1080 cells. As a result, the number of tumors and the tumor volume were significantly reduced in the single administration group of dry powders of ashwagandha leaves and in the co-administration group of dry powders of ashwagandha leaves and γ-cyclodextrin, in comparison to the control group.

INDUSTRIAL APPLICABILITY

By applying the preparation method of the present invention, it becomes possible to provide a water extract of ashwagandha leaves, in which the amounts of withanone and withaferin A contained as active ingredients therein have been increased. In addition, according to the present invention, it also becomes possible to more economically and simply provide a pharmaceutical composition comprising ashwagandha leaves.

All publications, patents and patent applications cited herein are incorporated herein by reference in their entirety.

We claim:

1. A method for treating or preventing cancer, which comprises extracting ashwagandha leaves with water in the presence of β-cyclodextrin to obtain a water extract of ashwagandha leaves and administrating the obtained water extract of ashwagandha leaves to a subject in need thereof.

2. A method for treating or preventing cancer, which comprises administrating a composition obtained by mixing a water extract of ashwagandha leaves with γ-cyclodextrin or administrating dry powders of ashwagandha leaves and γ-cyclodextrin simultaneously, separately or sequentially to a subject in need thereof.

* * * * *